(12) United States Patent
Rogers et al.

(10) Patent No.: US 8,939,963 B2
(45) Date of Patent: Jan. 27, 2015

(54) SURGICAL INSTRUMENTS WITH SHEATHED TENDONS

(75) Inventors: Theodore W. Rogers, Alameda, CA (US); John Ryan Steger, Sunnyvale, CA (US); Eugene F. Duval, Menlo Park, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 1651 days.

(21) Appl. No.: 12/346,402

(22) Filed: Dec. 30, 2008

(65) Prior Publication Data

US 2010/0168510 A1   Jul. 1, 2010

(51) Int. Cl.
| | | |
|---|---|---|
| *A61B 1/012* | (2006.01) | |
| *A61B 17/32* | (2006.01) | |
| *A61B 17/00* | (2006.01) | |
| *A61B 17/29* | (2006.01) | |
| *A61B 19/00* | (2006.01) | |
| *A61B 17/34* | (2006.01) | |

(52) U.S. Cl.
CPC ... *A61B 17/320016* (2013.01); *A61B 2017/003* (2013.01); *A61B 2017/2948* (2013.01); *A61B 2017/00845* (2013.01); *A61B 2017/2902* (2013.01); *A61B 2019/2242* (2013.01); *A61B 17/29* (2013.01); *A61B 2017/3441* (2013.01)
USPC .............. 606/1; 600/114; 604/516; 606/205; 606/170; 227/176.1; 74/490.04

(58) Field of Classification Search
CPC .......... A61B 1/04; A61B 17/00; A61B 17/32; A61B 17/04; A61M 31/00; B25J 18/00
USPC .............. 606/1, 170, 205, 208; 600/142, 146, 600/114; 227/179.1, 175.2, 176.1; 604/516; 74/490.04
See application file for complete search history.

(56) References Cited

U.S. PATENT DOCUMENTS

| | | | |
|---|---|---|---|
| 3,038,558 A | 12/1962 | Plummer | |
| 4,528,079 A | 7/1985 | Badger | |
| 4,826,481 A * | 5/1989 | Sacks et al. | 604/516 |

(Continued)

FOREIGN PATENT DOCUMENTS

| | | | | |
|---|---|---|---|---|
| EP | 1258229 A1 * | 11/2002 | | A61F 2/06 |
| GB | 1392717 A | 4/1975 | | |

(Continued)

OTHER PUBLICATIONS

Vertut, Jean et al., Robot Technology: Teleoperation and Robotics Evolution and Development, 1986, vol. 3A, 332 pages, English translation Prentice-Hall, Inc., Inglewood Cliffs, NJ, USA.

(Continued)

*Primary Examiner* — William Thomson
*Assistant Examiner* — Victor Shapiro

(57) ABSTRACT

A flexible surgical instrument employs sheaths around tendons that actuate an end effector or other mechanisms in a distal tip of the instrument. A liquid lubricant can be introduced in the sheaths to reduce friction, and the sheaths can be porous or non-porous. The lubricant can be confined, for example, with an o-ring or a bellow seal, to keep lubricant from leaking where the tendons extend out of the sheaths. More generally, the distal end of the instrument is sealed to prevent leakage of lubricant into a patient. To further reduce risks, a non-toxic water-based lubricant can be used.

25 Claims, 2 Drawing Sheets

(56) References Cited

U.S. PATENT DOCUMENTS

| | | | |
|---|---|---|---|
| 5,009,122 A | | 4/1991 | Chaczyk et al. |
| 5,133,727 A | * | 7/1992 | Bales et al. ............... 606/170 |
| 5,333,773 A | * | 8/1994 | Main et al. ............... 227/179.1 |
| 5,400,927 A | * | 3/1995 | Marchadour ............... 222/380 |
| 5,456,722 A | * | 10/1995 | McLeod et al. ............... 128/898 |
| 5,547,117 A | * | 8/1996 | Hamblin et al. ............ 227/175.2 |
| 5,559,087 A | | 9/1996 | Halsrud et al. |
| 5,586,968 A | * | 12/1996 | Grundl et al. ............... 600/114 |
| 5,618,291 A | | 4/1997 | Thompson et al. |
| 5,677,058 A | * | 10/1997 | Neal et al. ............... 428/375 |
| 5,808,665 A | | 9/1998 | Green |
| 5,814,058 A | * | 9/1998 | Carlson et al. ............... 606/185 |
| 5,829,754 A | * | 11/1998 | Preikschat ............... 277/408 |
| 5,855,311 A | * | 1/1999 | Hamblin et al. ............ 227/176.1 |
| 5,935,914 A | | 8/1999 | Theyssen et al. |
| 6,129,751 A | | 10/2000 | Lucchesi et al. |
| 6,327,841 B1 | | 12/2001 | Bertini et al. |
| 6,394,998 B1 | | 5/2002 | Wallace et al. |
| 6,603,993 B1 | | 8/2003 | Coutts et al. |
| 6,677,283 B2 | | 1/2004 | Ni |
| 6,746,443 B1 | | 6/2004 | Morley et al. |
| 6,763,914 B2 | | 7/2004 | Kuo |
| 6,817,974 B2 | * | 11/2004 | Cooper et al. ............... 600/142 |
| 6,840,127 B2 | * | 1/2005 | Moran ............... 74/490.04 |
| 6,858,005 B2 | | 2/2005 | Ohline et al. |
| 6,871,556 B2 | * | 3/2005 | Andresen et al. ............ 73/863.21 |
| 6,923,757 B2 | | 8/2005 | Abe et al. |
| 7,052,489 B2 | * | 5/2006 | Griego et al. ............... 606/1 |
| 7,060,199 B2 | | 6/2006 | Woydt et al. |
| 7,125,827 B2 | | 10/2006 | Li et al. |
| 7,172,552 B2 | * | 2/2007 | Wendlandt ............... 600/114 |
| 7,871,422 B2 | * | 1/2011 | Shibata ............... 606/205 |
| 2001/0047124 A1 | | 11/2001 | Yamamoto |
| 2005/0004432 A1 | * | 1/2005 | Suzuki et al. ............... 600/146 |
| 2005/0283224 A1 | * | 12/2005 | King ............... 623/1.13 |
| 2006/0111615 A1 | | 5/2006 | Danitz et al. |
| 2008/0065105 A1 | | 3/2008 | Larkin et al. |
| 2008/0154288 A1 | | 6/2008 | Belson |
| 2008/0255423 A1 | | 10/2008 | Kondo et al. |

FOREIGN PATENT DOCUMENTS

| | | |
|---|---|---|
| JP | S52124351 U | 9/1977 |
| JP | S5644216 U | 4/1981 |
| JP | S61108510 U | 7/1986 |
| JP | 2002530209 A | 9/2002 |
| JP | 2002537884 A | 11/2002 |
| JP | 2003325436 A | 11/2003 |
| JP | 2007527747 A | 10/2007 |
| WO | WO-9712557 A1 | 4/1997 |
| WO | WO-9712558 A1 | 4/1997 |
| WO | WO-0030557 A1 | 6/2000 |
| WO | WO-0051486 A1 | 9/2000 |
| WO | WO-2005084250 A2 | 9/2005 |

OTHER PUBLICATIONS

PCT/US09/68411 International Search Report and Written Opinion of the International Searching Authority, mailed Mar. 30, 2010, 10 pages.

PCT/US09/68416 International Search Report and Written Opinion of the International Searching Authority, mailed Mar. 30, 2010, 9 pages.

\* cited by examiner

SURGICAL INSTRUMENTS WITH SHEATHED TENDONS

CROSS-REFERENCE TO RELATED APPLICATION

This patent document is related to a co-filed U.S. patent application entitled "Lubricating Tendons in a Tendon-Actuated Surgical Instrument,", which is hereby incorporated by reference in its entirety.

BACKGROUND

Robotically controlled instruments are often used in minimally invasive surgical procedures. One common architecture for such surgical instruments includes an end effector or tool such as forceps, a scalpel, scissors, a wire loop, or a cauterizing tool mounted at the distal end of an extension, which is sometimes referred to herein as the main tube of the instrument. The distal tip of a robotically controlled instrument typically includes a wrist mechanism between the main tube and the end effector that allows for manipulating, positioning, or orienting the working surfaces of the end effector. During a surgical procedure, the end effector, the wrist mechanism, and the distal end of the main tube can be inserted through a small incision or a natural orifice of a patient and directed as needed to position the end effector at a work site within the body of the patient. Tendons, which can be cables or similar structures, extend through the main tube of the instrument and connect the end effector to a transmission and actuation mechanism, which is sometimes referred to herein as a backend mechanism. For robotic operation of the surgical instrument, the backend mechanism at the proximal end of the instrument is motor driven to pull on the tendons and thereby move or otherwise operate the wrist mechanism and end effector, and a computing system may be used to provide a user interface for a surgeon to precisely control the instrument.

Robotically controlled surgical instruments are being developed that have flexible main tubes that are able to bend as needed to follow a natural lumen such as a portion of the digestive tract of a patient or for insertion through a curved guide tube that provides an improved approach direction to the surgical site when compared to a straight approach. Whether inserted directly or through a guide, the main tubes of these flexible medical instruments will generally have several bends at locations that may vary during a procedure and may vary from one procedure to the next. At these bends, the tendons running through the instrument may rub against the inside wall of the main tube of the instrument and against each other, and friction generated due to these bends (sometimes referred to as capstan friction) can greatly increase the forces required to move the tendons to operate the wrist and end effector at the distal end of the main tube. Furthermore, these frictional forces tend to be higher at zero velocity than at low non-zero velocities, resulting in what is called stick-slip motion (sometimes referred to as stiction) in response to changes in tendon load. This stick-slip motion makes smooth robotic control of small motions of the instrument distal joints difficult to achieve. The large friction also makes construction of small-diameter flexible surgical instruments more difficult because mechanical structures must be designed to be robust enough to withstand the large forces. Accordingly, structures and methods for reducing the capstan friction encountered in flexible surgical instruments are desired.

SUMMARY

In accordance with an aspect of the invention, a surgical instrument with a flexible main tube employs sheaths around tendons that actuate an end effector or other mechanisms in the instrument. The sheaths add axial rigidity around the tendons to oppose the tendons' reactive forces and reduce or eliminate lateral movement of the tendons during actuation of the instrument. Additionally, a lubricant can be provided in the sheaths to reduce friction that opposes movement of the tendons. The sheaths can be porous to permit flow of lubricant between the interior and exterior of the sheaths, and the interior of the main tube can be filled with lubricant. Alternatively, the sheaths can be non-porous and sealed, for example, with a bellows-type seal, to keep lubricant within the sheaths. In either case, the distal end of the main tube and the sheaths are generally sealed to prevent leakage of lubricant into a patient. To further reduce risks, a surgically approved or biocompatible lubricant such as a lubricant that is composed of water and one to thirty percent (1-30%) by weight fatty acid or one to ten percent (1-10%) by weight refined mineral oil can be used.

One specific embodiment of the invention is a surgical system that may be robotically controlled. The system includes a bundle of sheaths with tendons respectively extending through the sheaths. A liquid lubricant is between the sheaths and the tendons, and a seal system is used to confine the liquid lubricant. A distal tip at an end of the bundle of sheaths is connected to the tendons so that movement of the tendons actuates the distal tip.

BRIEF DESCRIPTION OF THE DRAWINGS

Use of the same reference symbols in different figures indicates similar or identical items.

DETAILED DESCRIPTION

In accordance with an aspect of the current invention, a robotically controlled surgical instrument with a flexible main tube can employ liquid lubricants on tendons to reduce capstan friction at bends in the instrument. The lubricants can be in housings or sheaths that surround the medial portion of the tendons and extend through the main tube to actuated features of the instrument. Further, the main tube can contain lubricants to reduce friction caused by tendon sheaths rubbing against each other or against an inner wall of the main tube. The sheaths of the tendons can be porous to permit movement of lubricants between the interiors and exteriors of the sheaths or can be sealed to keep lubricants in the interior of the sheaths. Seals such as O-rings or bellows-type seals can keep lubricant with a sealed portion of the main tube or individual sheaths.

In accordance with another aspect of the invention, a flexible surgical instrument uses specific combinations of materials for structures such as main tubes, sheaths, and tendons and lubricants such as water-based solutions that together provide low friction and stiction and are not harmful to a patient undergoing a surgical procedure. One specific embodiment combines a stranded or braided tendon made of Ultra High Molecular Weight Polyethylene (UHMWPE) in a stainless steel sheath with a lubricant that is a mixture of water, a fatty acid or refined mineral oil, and a suitable surfactant.

Figure 1:
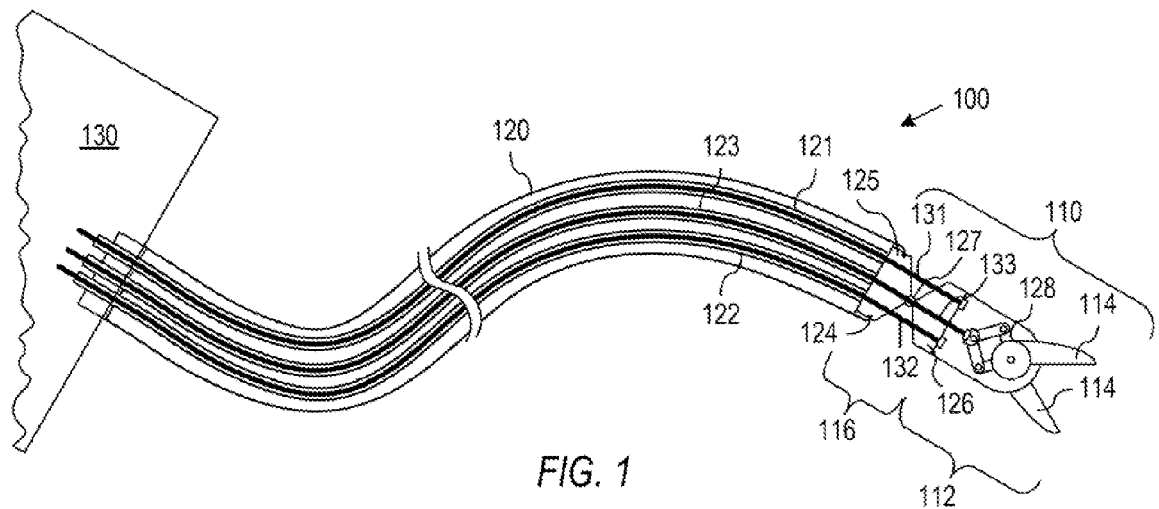
FIG. 1 shows a portion of a flexible surgical instrument in accordance with an embodiment of the invention employing tendons in sheaths and lubricant to reduce friction that resists movement of the tendons.

FIG. 1 illustrates a flexible surgical instrument 100 in accordance with an embodiment of the invention. Instrument 100 includes a backend mechanism 130, a flexible extension or main tube 120, and a distal tip section 110. For a surgical procedure, distal tip 110 and the distal end of main tube 120 can be inserted directly or through a guide to follow a curved path inside a patient to a site where a surgical procedure (or other medical or diagnostic procedure) may be performed. The path to the site may extend through an incision or through a natural orifice of a patient and along a natural lumen inside the patient. Portions of instrument 100 may further pass through an incision in the wall of the natural lumen to access the surgical site or further portions of the path that distal tip 110 must follow. In general, instrument 100 may need to follow a convoluted path including one or more bends. A process of inserting instrument 100 can be a manual process, such as currently performed for insertion of endoscopes or similar devices. Alternately, insertion may be fully robotically controlled or manually controlled but assisted by servo-actuated manipulation of joints in distal tip 110 or main tube 120. Once positioned for use at the surgical site, distal tip 110 can be used to perform surgical procedures, such as cutting, removal or destruction of tissue, insertion of medical devices, cauterization, vessel sealing, or suturing, to name a few.

Tendons 131, 132, and 133 extend from backend mechanism 130 and attach to distal tip 110 so that the tensions applied to tendons 131, 132, and 133 through backend mechanism 130 control operation of distal tip 110. Tendons 131, 132, and 133 can be of any suitable type that provides the strength and flexibility required for operation of distal tip 110. For example, tendons can be steel or other metal cables or tubes (e.g., hypotubes). Alternatively, each tendon 131, 132, or 133 can be a synthetic fiber or cable made of one or more materials such as UHMWPE, a Liquid Crystal Polymer (LCP), an aramid polymer (e.g., Kevlar), or poly(p-phenylene-2,6-benzobisoxazole) (PBO) to name a few suitable materials.

Distal tip 110 in the embodiment of FIG. 1 includes an end effector 112 and a wrist mechanism 116 that are actuated using tendons 131, 132, and 133. In particular, end effector 112 includes pivoting forceps-like jaws 114 that are actuated using tendons such as tendon 133. Tendon 133 provides a specific degree of freedom of motion to close jaws 114 for gripping, cutting, or other actions. Wrist mechanism 116 is actuated using tendons such as tendons 131 and 132 and provides specific degrees of freedom of motion to position and orient end effector 112. This specific function of distal tip 110 and arrangement and connection of tendons 131, 132, and 133 is provided only as an example for illustration of an embodiment of the invention. Other embodiments of the invention can employ other types of end effectors or wrist mechanisms or actuated main tubes that would benefit from reduction in tendon friction.

The connections of tendons 131, 132, and 133 to distal tip 110 illustrate structures and methods for actuation of a surgical instrument. To illustrate one strategy for actuating end effector 112, tendon 133 is shown connecting to jaws 114 such that tension in tendon 133 causes jaws 114 to close against one another. To illustrate one strategy for bi-directional actuation of wrist mechanism 116, tendons 131 and 132 are shown. In particular, tendons 131 and 132 attach to a wrist segment 126 at moment arms about a pivot axis 127 such that tension in tendon 131 causes a torque that tends to rotate wrist segment 126 in one direction (counterclockwise in FIG. 1) and tension in tendon 132 causes a torque that tends to rotate wrist segment 126 in the opposite direction (or clockwise in FIG. 1). Accordingly, end effector 112 can be oriented in one direction or another by pulling in a length of one tendon 131 or 132 while simultaneously releasing an equal length of the other tendon 132 or 131. Other strategies for actuation of portions of wrist mechanism 116 and end effector 112 using tendons could be employed. For example, three tendons (not shown) can be used to fully define the orientation of a wrist mechanism consisting of two non-redundant degrees of freedom. An actual medical instrument would generally require more tendons than are illustrated in FIG. 1 for actuation of a suitable number of degrees of freedom in a surgical instrument, but only three tendons 131, 132, and 133 are shown in FIG. 1 for ease of illustration. Many types of end effectors and wrist mechanisms are known in the art, and some examples of a few such mechanisms are described in U.S. Pat. App. Pub. No. US 2008/0065105, entitled "Minimally Invasive Surgical System," to Larkin et al.; U.S. Pat. No. 6,746,443, entitled "Roll-Pitch-Roll Surgical Tool," to Morley et al.; and U.S. Pat. No. 6,394,998, entitled "Surgical Tools for use in Minimally Invasive Telesurgical Applications," to Wallace et al., which are hereby incorporated by reference in their entirety.

Backend mechanism 130 serves as a transmission that can be connected to drive motors and a computer aided control system (not shown) that control the tension in tendons 131, 132, and 133 as needed to operate instrument 100. In general, the particular operation of backend mechanism 130 will depend on the actuation strategy employed in distal tip 110 or elsewhere in instrument 100. Implementations suitable for backend mechanisms 130 are known in the art and are not critical to use of embodiments of the current invention. Some examples of suitable backend mechanism are described in U.S. patent application Ser. No. 12/173,928, entitled "Backend Mechanism for Four Cable Wrist," of William A. Burbank; and U.S. patent application Ser. No. 12/286,644, entitled "Passive Preload and Capstan Drive for Surgical Instruments," of Giuseppe M. Prisco, which are hereby incorporated by reference in their entirety.

Main tube 120 is flexible as needed to follow a desired path to a surgical site as described above. In one embodiment, main tube 120 can be a uniform tube of a suitably flexible material such as Nylon, polyamide, silicone, or fluorinated ethylene propylene. Main tube 120 could additionally or alternatively be constructed of one or more layers of helical wire coil or a series of rigid rings or other structures that can move relative to each other in the manner of vertebrae. Such vertebrae can be made of plastic, metal, or other material that provides the required strength and durability of use in main tube 120. Main tube 120 can also be made as a composite material with multiple layers that could include low friction hydrophilic external coatings to allow for easy insertion through biological tissue, one or more internal reinforcement layers made from helical, woven, or braided strands of material such as stainless steel or synthetic high strength polymer fiber, a binding polymer surrounding the internal reinforcement layers, and a possible low friction inner wall coating such as PTFE. Main tube 120 can be constructed as a single lumen tube with all instrument sheaths bundled inside, or alternately, main tube 120 can be constructed as a multi-lumen tube with multiple passages to constrain individual or bundles of actuation cables in specific locations on the cross section of main tube 120. Additionally, main tube 120 can contain features that provide specific surgical functionality such as passages for insufflation, suction, surgical site irrigation, light or power delivery, and mechanisms for selectively changing the stiffness of the flexible portion of the main tube or actuating additional degrees of freedom on the main tube that are not part of distal tip 110.

In accordance with an aspect of the current invention, tendons 131, 132, and 133 are respectively enclosed in sheaths 121, 122, and 123 inside of main tube 120. Sheaths 121, 122, and 123 serve several purposes in instrument 100. In particular, sheaths 121, 122, and 123 are designed to have higher axial stiffness than tendons 131, 132, and 133 in order to resist reactive forces and lateral movement of tendons 131, 132, and 133 inside main tube 120 when backend mechanism 130 applies or changes tensions to tendons 131, 132, and 133. Sheaths 121, 122, and 123 can be made of metal such as Stainless Steel (e.g., 304, 17-4PH, Nitronic60®) or nickel-titanium alloy or a synthetic or polymer material such as Polyetheretherketone (PEEK), polyether block amide (PEBA) such as Pebax®, nylon, or polyimide. Sheaths 121, 122, and 123 can have a smooth/polished inner surfaces and de-burred ends to reduce the sliding friction of tendons 131, 132, and 133, but sheaths 121, 122, and 123 also contain liquid lubricant that further reduces friction encountered when backend mechanism moves tendons 131, 132, and 133 for operation of distal tip 110. Sheaths 121, 122, and 123 can either be porous to permit lubricant to pass between the interiors and exteriors of sheaths 121, 122, and 123 or non-porous to trap lubricant inside of sheaths 121, 122, and 123. Whether sheaths 121, 122, and 123 are porous or non-porous, the exterior of sheaths 121, 122, 123 can be coated with a liquid lubricant or the interior of main tube 120 can be filled with lubricant to reduce friction associated with sheaths 121, 122, and 123 sliding against each other, which would commonly occur when bending main tube 120 during insertion for a surgical procedure or otherwise.

A flexible surgical instrument with tendons 131, 132, and 133 in sheaths 121, 122, and 123 does not necessarily require main tube 120, but instead can use another mechanism to keep sheaths 121, 122, and 123 together during insertion. For example, ties, links, or other attachments (not shown) can be periodically positioned along the lengths of sheaths 121, 122, and 123 to hold the sheaths together. In other embodiments, a surgical instrument used with a separate guide can employ sheaths 121, 122, and 123 and tendons 131, 132, and 133 without main tube 120 or attachment of sheaths 121, 122, and 123, and a lumen in the guide can keep sheaths 121, 122, and 123 bundled together.

Tendons 131, 132, and 133 extend beyond the ends of respective sheaths 121, 122, and 123 to make connections to actuated components, and seals can be employed to confine lubricants in the desired portion or portions of instrument 100 even though tendons 131, 132, and 133 extend beyond the portions where lubricant is confined. For example, a compression seal 124 can seal main tube 120 against a member 125 of wrist mechanism 116, and individual seals can be positioned at the ends of sheaths 121, 122, and 123 that contact member 125. Confining liquid lubricants in main tube 120 or in sheaths 121, 122, and 123 is generally desirable to avoid loss of lubricant where lubricant is needed and to minimize release of the lubricant in a patient during a surgical procedure. In any case, the chosen lubricant should not be harmful to the patient because some leakage of lubrication during a surgical procedure may be anticipated as a result of normal operations or malfunctions of instrument 100.

Figure 2:
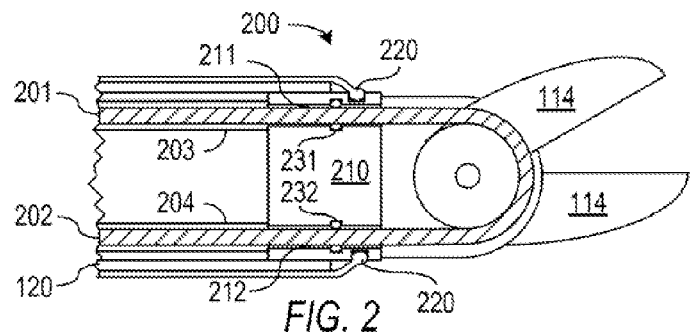
FIG. 2 shows the distal end of a surgical instrument in accordance with an embodiment of the invention using o-rings to seal guides through which tendons leave a sealed portion of the main tube.

FIG. 2 shows a portion of an end effector 200 at the distal end of a main tube 120 of a flexible surgical instrument similar to instrument 100 of FIG. 1. End effector 200 employs a base member 210 that fits within main tube 120, a seal 220 preventing leakage from between main tube 120 and member 210, and seals 231 and 232 preventing leakage from around tendons 201 and 202 that extend from main tube 120. More generally, a seal system at the distal end of an actuated instrument would need to seal each tendon that extends outside the volume in which lubricant is confined, so that more than the two seals 231 and 232 would be needed in a typical flexible instrument. The proximal end (not shown in FIG. 2) of main tube 120 attaches to a backend mechanism such as described above and may similarly include seals to confine lubricants in main tube 120 or may include a system for injecting lubricants into or circulating lubricants within main tube 120.

Member 210 has a portion that fits within main tube 120 of the instrument and a portion that extends beyond main tube 120. In the illustrated embodiment, the portion of member 210 that extends beyond main tube 120 provides a surface that seal 220 engages. Seal 220 can be an O-ring or compression ring that may be part of a sheath that extends the length of main tube 120 or a part of a boot that fits over the end of main tube 120. Alternatively, a sealing material or an adhesive can be applied between member 210 and main tube 120 to prevent lubricant leakage.

Seals 231 and 232 are O-rings that are positioned in guide tubes 211 and 212 that extend through member 210. Tendons 201 and 202 run through guide tubes 211 and 212 and tightly fit through respective seals 231 and 232, so that seals 231 and 232 are compressed between respective tendons 201 and 202 and the interior wall of respective guide tubes 211 and 212. Each guide tube 211 or 212 may include a notch or other structure that holds the corresponding seal 231 or 232 in place when tendons 201 and 202 move for actuation of end effector 200. As a result, tendons 201 and 202 can slide against seals 231 and 232 without causing significant leakage of lubricant. If desired, the material or structure of tendons 201 and 202 can be different in areas where tendons 201 and 202 contact respective seals 231 and 232. For example, a tendon 201 or 202 can include a portion of synthetic cable that is used to provide flexibility along most of the length of main tube 120 fused to a portion of metal or plastic tube or rod to provide a better sealing surface where the tendon 201 or 202 contacts the corresponding seal 231 or 232. Additionally, employing a solid rod as part of tendon 201 or 202 can act as a seal to minimize wicking of lubricant, which can occur particularly for stranded synthetic cable. Alternatively, a flexible sealing material, such as a liquid silicone or urethane, that penetrates a cable and bonds to the fibers of the cable can prevent wicking, and the flexible sealing material can be molded or otherwise formed prior to curing to create a smooth surface around an otherwise non-smooth cable and thereby improve seal performance of o-ring seals 231 and 232.

Figure 3:
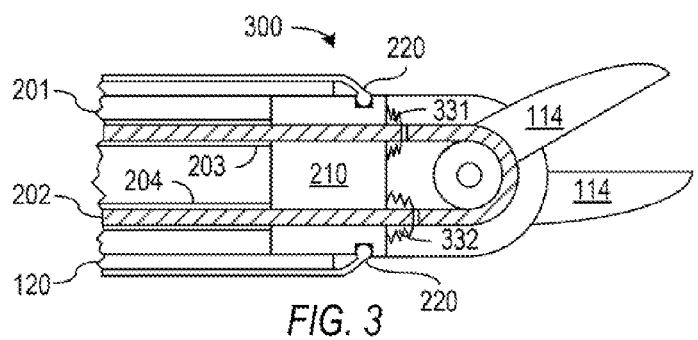
FIG. 3 shows the distal end of a surgical instrument in accordance with an embodiment of the invention using bellows-type seals to cap guides through which tendons leave a sealed portion of the main tube.

FIG. 3 illustrates an end effector 300 that is similar to end effector 200 of FIG. 2, but end effector 300 uses accordion or bellows-type seals 331 and 332 for preventing leakage from around respective tendons 201 and 202. Each seal 331 or 332 has one end that can be glued or otherwise affixed to mechanical member 210 and an opposite end that can be glued or otherwise affixed to the corresponding tendon 201 or 201. Each seal 331 or 332 has folds of a resilient material that fold or unfold as the attached tendon 201 or 202 moves. Permanently affixing the ends of each seal 331 and 332 prevents wear of seal 331 or 332 caused by tendon 201 or 202 rubbing against a fixed seal. Seals 331 and 332 of end effector 300 may have less lubricant leakage, create fewer particulates as a result of wear, and have a longer life than seals 231 and 232, which rub against tendons 201 and 202. However, seals 231 and 232 may require less space and facilitate implementation of smaller diameter instruments.

The seal systems of FIGS. 2 and 3 can prevent or minimize leakage of liquid lubricant at the distal end of main tube 120 and thus permit main tube 120 to contain or be filled with lubricant. In one embodiment of the invention, the sheaths 203 and 204 of tendons 201 and 202 are porous so that lubricant can pass between the interior and the exterior of each sheath 203 or 204. If sheaths 203 and 204 have a low level of porosity, sheaths 203 and 204 can be filled with lubricant that seeps to the exterior surface of sheaths 203 and 204. The lubricant inside sheaths 203 and 204 decreases friction between tendons 201 and 202 and respective sheaths 203 and 204 when tendons 201 and 202 move. Lubricant coated externally on sheaths 203 and 204 decreases friction amongst sheaths 203 and 204 and main tube 120 when sheaths 203 and 204 move during bending of flexible main tube 120. If sheaths 203 and 204 have a high level of porosity, lubricant can fill main tube 120 and sheaths 203 and 204 to similarly prevent friction.

Figure 4:
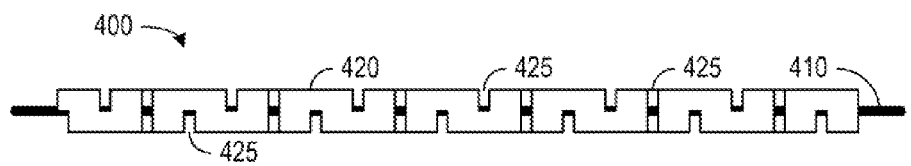
FIG. 4 shows a sheathed tendon in accordance with an embodiment of the invention in which slots or kerfs in the sheath make the sheath more flexible and porous to lubricant.

Sheaths 203 and 204 can be made porous through selection of a material for sheaths 203 and 204 that is permeable to the lubricant or by making holes (e.g., pin holes or kerfs) in a non-permeable sheath material at intervals along the length of each sheath 203 or 204. Another type of porous sheath 203 or 204 uses a helical wound wire that permits flow of lubricant between coils of the wire. Yet another type of porous sheath is a tube made from strands that are woven so that lubricant can pass between the strands. FIG. 4 shows a tendon-sheath system 400 including a tendon 410 running through a sheath 420 that includes a series of kerfs 425. Kerfs 425 provide fluid paths between the interior and exterior of sheath 420 and can also increase the flexibility of sheath 420, so that sheath 420 can be made of a relatively rigid material such as stainless steel.

Figure 5A:
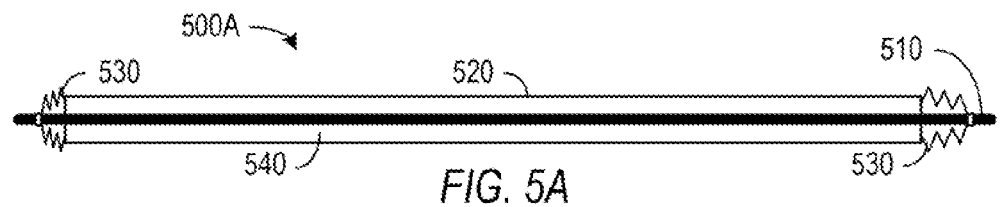
FIGS. 5A and 5B shows sheathed tendons in accordance with embodiments of the invention using end seals to keep lubricant within the sheaths.
Figure 5B:
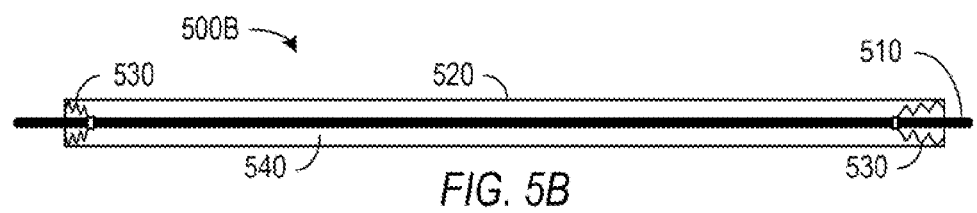

An alternative system for confining lubricants to desired areas uses non-porous sheaths that can be sealed to confine lubricants to the interior of the sheaths. FIG. 5A shows an example of a sheath-tendon system 500A including a tendon 510 in a sheath 520. Sheath 520 in this system is non-porous and may be, for example, a stainless steel hypotube, a plastic tube, or a helical coil of wire within a polyamide, polyimide, polyether block amide matrix, or other non-porous coating. A stranded-swaged metal tube such as sold commercially by Fort Wayne Metals or Asahi-Intec (Japan) can provide a non-porous sheath with the friction characteristics of a hypotube but with greater flexibility. If desired, sheath 520 can be a multi-part sheath that combines a solid hypotube for a back-end section having lower flexibility and a stranded-swaged metal tube for a highly flexible section near the distal tip. Seals 530 are at both ends of sheath 520 to confine a liquid lubricant 540 to the interior of sheath 520. In the illustrated embodiment, seals 530 are bellows-type seals with ends respectively affixed to tendon 510 and sheath 520, but alternatively, O-rings or any other type of seal that confines lubricant 540 but permits movement of tendon 510 relative to sheath 520 could be used. FIG. 5A illustrates one specific configuration of seals 530 that are bellows-type seals and outside of sheath 520 at both ends. Other configurations are also possible. FIG. 5B, for example, shows a configuration in which both bellows-type seals 530 are in the interior of sheath 520. Alternatively, a tendon seal 530 may be used at only one end of each sheath 520, for example, at the proximal end while the distal end of sheaths and tendons can attach to a distal tip having seals of the types described above with reference to FIGS. 2 and 3.

The lubricant employed in a particular flexible instrument will generally be chosen according to the materials used in the tendons, sheaths, and main tube of the instrument and to a lesser extent on the dimensions of the components. For example, a lubricant that is an aqueous solution containing a fatty acid is an excellent lubricant between a metal tendon and a metal sheath, and an aqueous solution of mineral oil is an excellent lubricant between a synthetic tendon and a metal sheath. In one exemplary implementation, the tendons are stranded or braided UHMWPE with a diameter of about 0.4 mm inside a sheath that is a stainless steel hypotube having an inner diameter of about 0.5 mm. For enhanced strength and stiffness, each tendon could contain a more complex structure such as a tubular braid of ultra high molecular weight polyethylene fibers surrounding an inner core of poly(p-phenylene-2,6-benzobisoxazole) fibers. Surface strands in each tendon can be partially fused if desired to provide a smooth outer surface for the tendon. A water-based lubricant that contains up to ten percent (10%) and preferably about five percent (5%) or more refined medicinal grade mineral oil or up to thirty percent (30%) and preferably about five percent (5%) or more fatty acid such as lauric or myristic acid can be allowed to saturate the tendon (e.g., a braided or stranded tendon) prior to or after feeding the tendon through the sheath. The lubricant may also contain a surfactant such as a trisiloxane, in a concentration of 0.05-1% to aid in creating an aqueous solution of the fatty acid or mineral oil. These lubricant formulations provide a low coefficient of friction for this combination of tendon-sheath materials, without being harmful to a patient during surgery in the event of leakage of lubricant.

Other lubricant formulations could also be used, for example, aqueous solutions with higher percentages of mineral oil or a fatty acid up to the limits of solubility in water of the carbon-based lubricants. Additionally, these lubricants can dry out over time thereby changing the relative proportion of water, but even after drying out the lubricants still provide a lubricating function as desired. Pure water or pure mineral oil could also be used. A saline solution, e.g., a normal saline solution with 0.9% by weight of sodium chloride (NaCl) in water, is a medically safe liquid lubricant that can also provide reduced friction without stick-slip motion when used with synthetic tendons (e.g., UHMWPE tendons) in metal sheaths, e.g., stainless steel sheaths.

The combination of sheath material and tendon material is important for providing low friction and avoiding stick-slip motion. For the exemplary embodiment using UHMWPE tendons and stainless steel sheaths, specific types of stainless steel such as 17-4 PH, Nitronic 60, or 304 may provide better results (i.e., lower friction) than do other types of stainless steel.

In other embodiments, other metals or high strength polymers may be substituted for the stainless steel in the sheath material. Sheaths constructed of different materials generally require different lubricant formulations for optimal performance. For example, tendons constructed of braided UHMWPE could be used inside a sheath constructed of polyetheretherketone (PEEK) or polyamide-imide (PAI) combined with a water-based lubricant containing 1-30% of a dissolved fatty acid such as lauric or myristic acid. UHMWPE tendons could also be used in superelastic nickel-titanium alloy (Nitinol®)

sheaths with a liquid lubricant of the types described above used to achieve low friction and avoid stick-slip motion.

If it is desired to have a lubricant that is less susceptible to drying out during storage or manufacture than are the water-based lubricants previously described, a polyglycol such as polyethylene glycol (PEG) can be substituted for the water base in the lubricant. In an exemplary embodiment, a lubricant for UHMWPE tendons contained in stainless steel sheaths can be made from a base of polyethylene glycol (PEG) containing one to six (1-6%) of a dissolved fatty acid such as lauric acid or myristic acid.

the wrist mechanism on the distal tip of the instrument. The tendons connecting to these mechanical linkages typically pass over or through the linkage components, thereby creating friction at interfaces where the tendons slide on the mechanical linkages. In addition to satisfying other design and performance constraints of the instrument distal tip, proper selection of combinations of materials or applied lubricant at these locations can achieve a low coefficient of friction with little to no stick-slip behavior.

Table 2 shows some material choices for lubricants and mechanical components when the distal mechanism is sub-

TABLE 1

Material and Lubricant Combinations for Sheathed Tendons

| Sheath Material | Tendon Material | Lubricant Base | Fatty-Acid (≤30%) | Mineral Oil (≤10%) | Surfactant (0.05-1%) |
|---|---|---|---|---|---|
| Stainless Steel (e.g., 304, 17-4PH, Nitronic60 ®) | UHMWPE fiber or a UHMWPE fiber composite containing other synthetic fibers (e.g. PBO, LCP, Aramid) | (none) | | | |
| | | Water or Saline (NS) | | | |
| | | Water | X | | |
| | | Water | X | | X |
| | | Water | X | X | X |
| | | Water | | X | X |
| | | Mineral oil | | | |
| | | Mineral oil | | | X |
| | | Polyethylene Glycol (PEG) | | | |
| | | Polyethylene Glycol (PEG) | X | | |
| | | Polyethylene Glycol (PEG) | X | | X |
| Polymer (PEEK, Pebax ®, Nylon, or Polyimide) | | Water | X | | |
| | | Water | X | | X |
| | | Water | X | X | X |
| | | Water | | X | X |
| | | Mineral oil | | | |
| | | Mineral oil | | | X |

Table 1 shows several combinations of sheath material, tendon material, and lubricant formulations that, in correct application, have been shown to provide little to no stick-slip behavior and friction coefficients sufficiently low to enable smooth control of flexible bodied robotically driven surgical instruments. Each lubricant listed in Table 1 indicates a base for the lubricant and designates which if any of the listed additives are contained in the lubricant. Table 1 presents an overview of suitable material combinations, however the optimal selection of tendon material, sheath material, and lubricant can vary with the specific design parameters of a surgical tool, and particularly on the intended use, cost, and life cycle of the surgical tool.

The distal end of the robotically controlled surgical instrument typically contains mechanical linkages that convert the reaction force between the tendon and the sheath into a mechanical action that articulates a component of the distal tip. Examples of this mechanical action include opening and closing an end effector jaw and pivoting joints that comprise ject to friction due to tendons sliding over the surfaces of the mechanical components. Each lubricant listed in Table 2 indicates a base for the lubricant and designates which if any of the listed additives are contained in the lubricant. Table 2 presents an overview of suitable material combinations, however the optimal selection of tendon material, mechanical component material, and lubricant can vary with the specific design parameters of a surgical tool, and particularly on the intended use, cost, and life cycle of the surgical tool. In general, the mechanical components need to be made of a metal or suitably strong synthetic material such as Polyamide-imide (PAI), mica-reinforced poly(tetrafluoroethylene) (PTFE), polybenzamidazole (PBI), polyparaphenyl copolymer (PPP), Polyetheretherketone (PEEK) that may be neat, glass, or carbon filled. Table 2 only shows the example of synthetic tendons but a metal tendon might alternatively be used.

TABLE 2

Material and Lubricant Combinations for Tendons sliding on Mechanical Components.

| Tendon Material | Mechanical Component Material | Lubricant Base | Fatty-Acid (≤30%) | Mineral Oil (≤10%) | Surfactant (0.05-1%) |
|---|---|---|---|---|---|
| UHMWPE fiber or a UHMWPE composite | Stainless Steel (e.g., 304, 17-4PH, | (none) | | | |
| | | Water or Saline (NS) | | | |
| | | Water | X | | |

TABLE 2-continued

Material and Lubricant Combinations for Tendons sliding on Mechanical Components.

| Tendon Material | Mechanical Component Material | Lubricant Base | Fatty-Acid (≤30%) | Mineral Oil (≤10%) | Surfactant (0.05-1%) |
|---|---|---|---|---|---|
| containing other synthetic fibers (e.g. PBO, LCP, Aramid) | Nitronic60 ® | Water | X | | X |
| | | Water | X | X | X |
| | | Water | | X | X |
| | | Mineral oil | | | |
| | | Mineral oil | | | X |
| | | Polyethylene Glycol PEG) | | | |
| | | Polyethylene Glycol (PEG) | X | | |
| | | Polyethylene Glycol (PEG) | X | | X |
| | Polyamide-imide (PAI) (neat, glass, or carbon filled) | Water | X | | |
| | | Water | | X | X |
| | Mica-reinforced | (none) | | | |
| | | Water | X | | |
| | PTFE (Fluorosint ®) | Water | | X | X |
| | PBI (Celazole ®) | Water | | X | X |
| | PPP (Tecamax ®) | Mineral oil | | | |
| | PEEK (neat, glass filled), (carbon filled) | Water | X | | |
| | | Water | X | | X |
| | | Water | X | X | X |
| | | Water | | X | X |
| | | Mineral oil | | | |
| | | Mineral oil | | | X |

Figure 6:
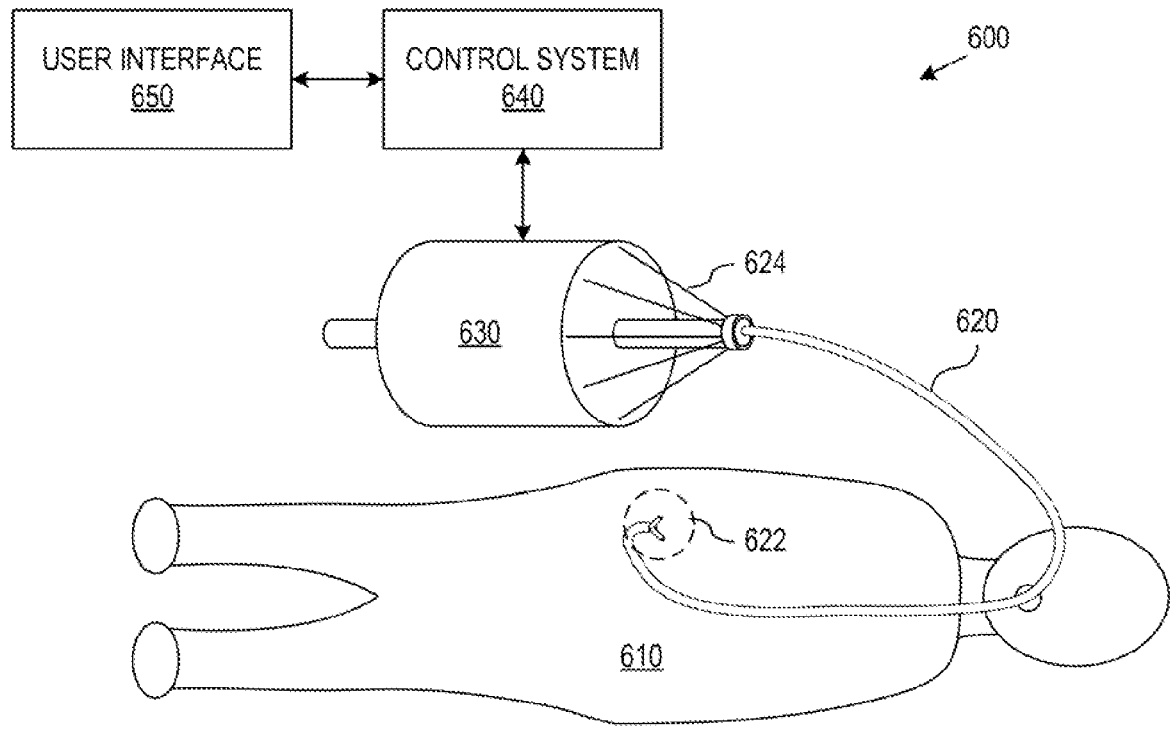
FIG. 6 illustrates an application of a flexible, robotically-controlled surgical instrument in accordance with an embodiment of the invention.

FIG. 6 illustrates a system 600 for performing a minimally invasive surgical procedure on a patient 610. System 600 employs a flexible main tube 620 that can be inserted though a natural orifice, such as the mouth of patient 610, and directed along a natural lumen, such as the digestive tract of patient 610. Alternatively, main tube 620 can follow the path of a guide (not shown) which may be inserted along the desired path in patient 610 before main tube 620 is inserted into the guide. An actuated tip 622 at the distal end of main tube 620 is operated using tendons 624. The actuation of distal tip 622 can occur when the distal end of main tube 620 reaches the surgical site in patient 610 or during the insertion process, for example, when making an incision in the wall of the natural lumen in order to facilitate access by main tube 620 of a work site outside the natural lumen.

Tendons 624, which can be used for control of distal tip 622 and control of the position or shape of entry guide 620, run through lubricated sheaths (not shown) inside main tube 620 and connect to an actuator package 630 that controls the tensions in tendons 624 as required for operation of system 600. An interface for sensor signals and video signals from main tube 620 may be provided through actuator package 630, a control system 640, or a user interface 650. Electrical or other power and communication signals could also be sent to or received from sensors or control electronics at distal tip 622. User interface 650 preferably provides an operator, e.g., a surgeon, with a visual display such as a stereoscopic (3-D) display and includes manipulator controls that the operator moves to guide distal tip 622. Control system 640 can convert the surgeon's movements of the manipulator controls in user interface 650 into control signals that cause actuator package 630 to apply tension to cables 624 as necessary to cause the desired movement of distal tip 622 or main tube 620. Some suitable user interfaces and control systems are further described in U.S. Pat. No. 5,808,665, entitled "Endoscopic Surgical Instrument and Method for Use," which is hereby incorporated by reference in its entirety.

Although the invention has been described with reference to particular embodiments, the description is only an example of the invention's application and should not be taken as a limitation. Various adaptations and combinations of features of the embodiments disclosed are within the scope of the invention as defined by the following claims.

What is claimed is:

1. A surgical system comprising:
   a bundle of sheaths;
   a plurality of tendons respectively extending through the sheaths;
   a liquid lubricant between the sheaths and the tendons respectively extending through the sheaths;
   a seal system that seals around each of the plurality of the tendons and confines the liquid lubricant; and
   a distal tip at an end of the bundle of the sheaths and connected to the tendons so that movement of the tendons actuates the distal tip.

2. The system of claim 1, further comprising a main tube through which the sheaths extend.

3. The system of claim 2, wherein each of the sheaths is porous to permit flow of the liquid lubricant between an interior and an exterior of the sheath.

4. The system of claim 2, wherein each sheath comprises a tube in which kerfs are cut.

5. The system of claim 2, wherein each sheath comprises a tube with a plurality of holes through a wall of the tube.

6. The system of claim 2, wherein each sheath comprises a tube made of woven strands.

7. The system of claim 2, wherein each sheath comprises a tube made of helically wound strands.

8. The system of claim 2, wherein the main tube is filled with the liquid lubricant and the seal system confines the liquid lubricant in the main tube.

9. The system of claim 1, wherein the sheaths are non-porous to the liquid lubricant.

10. The system of claim 1, wherein the seal system comprises a plurality of first seals through which the tendons respectively pass, wherein the first seals inhibit leakage of the liquid lubricant from around the tendons.

11. The system of claim 10, wherein each of the seals comprises an o-ring.

12. The system of claim 10, wherein each of the seals comprises a bellows-type seal.

13. The system of claim 1, wherein each of the tendons comprises a synthetic fiber.

14. The system of claim 13, wherein each of the tendons comprises braided strands of ultra high molecular weight polyethylene.

15. The system of claim 13, wherein the braided strands of ultra high molecular weight polyethylene are partially fused to provide a smooth outer surface.

16. The system of claim 13, wherein each of the tendons comprises a tubular braid of ultra high molecular weight polyethylene fibers surrounding an inner core of poly(p-phenylene-2,6-benzobisoxazole) fibers.

17. The system of claim 1, wherein the sheaths comprise stainless steel.

18. The system of claim 1, wherein the sheaths comprise a composite construction of helically wound stainless steel embedded in a synthetic matrix.

19. The system of claim 1, wherein:
the sheaths are made of a metal; and
the tendons are made of a synthetic material.

20. The system of claim 19, wherein the metal is stainless steel.

21. The system of claim 20, wherein the synthetic material is selected from the group consisting of Ultra High Molecular Weight Polyethylene (UHMWPE), a Liquid Crystal Polymer (LCP), an aramid polymer, and poly(p-phenylene-2,6-benzobisoxazole) (PBO).

22. The system of claim 1, wherein the lubricant comprises an aqueous solution containing an additive selected from the group consisting of mineral oil, a fatty acid, and a surfactant.

23. The system of claim 1, wherein the liquid lubricant comprises polyethylene glycol.

24. The system of claim 23, wherein the liquid lubricant comprises an additive selected from the group consisting of a fatty acid and a surfactant.

25. The system of claim 1, wherein the distal tip, comprises:
a wrist mechanism including one or more joints, each of the joints providing at least one degree of freedom of motion that is actuated through movement of one or more of the tendons; and
an end effector mounted on the wrist mechanism and actuated by one or more of the tendons.

* * * * *